United States Patent
Hennings et al.

(10) Patent No.: US 9,782,222 B2
(45) Date of Patent: *Oct. 10, 2017

(54) SYSTEM AND METHOD FOR ENDOVENOUS TREATMENT OF VARICOSE VEINS WITH MID INFRARED LASER

(75) Inventors: David R. Hennings, Roseville, CA (US); Mitchell P. Goldman, La Jolla, CA (US); Robert A. Weiss, Hunt Valley, MD (US); Eric B. Taylor, Roseville, CA (US); Don Johnson, Roseville, CA (US)

(73) Assignee: COOL TOUCH INCORPORATED, Roseville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/604,815

(22) Filed: Oct. 23, 2009

(65) Prior Publication Data

US 2010/0042085 A1 Feb. 18, 2010

Related U.S. Application Data

(63) Continuation of application No. 10/699,212, filed on Oct. 30, 2003, now abandoned.

(Continued)

(51) Int. Cl.
*A61N 5/067* (2006.01)
*A61B 18/24* (2006.01)
(Continued)

(52) U.S. Cl.
CPC .... *A61B 18/24* (2013.01); *A61B 2017/00084* (2013.01); *A61B 2018/00005* (2013.01);
(Continued)

(58) Field of Classification Search
CPC .............................. A61B 18/203; A61B 18/24
(Continued)

(56) References Cited

U.S. PATENT DOCUMENTS

| | | | |
|---|---|---|---|
| 4,233,991 A | 11/1980 | Bradley et al. | |
| 4,672,969 A * | 6/1987 | Dew | 607/89 |

(Continued)

OTHER PUBLICATIONS

Jacques; Skin Optics; Oregon Medical Laser Cent News; http://omlc.ogi.edu/news/jan98/skinoptics.html; Jan. 1998; 8 pages.

(Continued)

*Primary Examiner* — Ahmed Farah
(74) *Attorney, Agent, or Firm* — Vorys, Sater, Seymour and Pease LLP; William L. Klima

(57) ABSTRACT

This invention is an improved method and device for treating varicose veins 200 or the greater saphenous vein 202. The method comprises the use of infrared laser radiation in the region of 1.2 to 1.8 um in a manner from inside the vessel 200 or 202 such that the endothelial cells of the vessel wall 704 are damaged and collagen fibers in the vessel wall 704 are heated to the point where they permanently contract, the vessel 200 or 202 is occluded and ultimately resorbed. The device includes a laser 102 delivered via a fiber optic catheter 300 that may have frosted or diffusing fiber tips 308. A motorized pull-back device 104 is used, and a thermal sensor 600 may be used to help control the power required to maintain the proper treatment temperature.

22 Claims, 12 Drawing Sheets

Related U.S. Application Data

(60) Provisional application No. 60/422,566, filed on Oct. 31, 2002.

(51) Int. Cl.
  *A61B 17/00* (2006.01)
  *A61B 18/00* (2006.01)
  *A61B 18/22* (2006.01)
  *A61B 90/00* (2016.01)

(52) U.S. Cl.
  CPC ............... *A61B 2018/00196* (2013.01); *A61B 2018/2261* (2013.01); *A61B 2090/036* (2016.02)

(58) Field of Classification Search
  USPC ....... 606/2–15; 128/898; 607/88, 89, 92, 96, 607/100
  See application file for complete search history.

(56) References Cited

U.S. PATENT DOCUMENTS

| | | | |
|---|---|---|---|
| 4,899,741 A | 2/1990 | Bentley et al. | |
| 5,022,399 A | 6/1991 | Biegeleisen | |
| 5,707,403 A | 1/1998 | Grove et al. | |
| 5,789,755 A | 8/1998 | Bender | |
| 5,810,801 A | 9/1998 | Anderson et al. | |
| 5,820,626 A | 10/1998 | Baumgardner | |
| 5,885,274 A | 3/1999 | Fullmer et al. | |
| 5,968,034 A | 10/1999 | Fullmer et al. | |
| 5,976,123 A | 11/1999 | Baumgardner et al. | |
| 5,984,915 A | 11/1999 | Loeb et al. | |
| 5,997,531 A * | 12/1999 | Loeb .................. | A61B 18/24 606/13 |
| 6,014,589 A | 1/2000 | Farley et al. | |
| 6,028,316 A | 2/2000 | Bender | |
| 6,033,398 A | 3/2000 | Farley et al. | |
| 6,083,223 A | 7/2000 | Baker | |
| 6,096,029 A * | 8/2000 | O'Donnell, Jr. ...... | A61B 18/203 606/3 |
| 6,117,335 A | 9/2000 | Bender | |
| 6,135,997 A | 10/2000 | Laufer et al. | |
| 6,139,527 A | 10/2000 | Laufer et al. | |
| 6,176,854 B1 * | 1/2001 | Cone ............................ 606/15 | |
| 6,197,020 B1 | 3/2001 | O'Donnell, Jr. | |
| 6,200,332 B1 | 3/2001 | Del Giglio | |
| 6,224,593 B1 | 5/2001 | Ryan et al. | |
| 6,228,078 B1 | 5/2001 | Eggers et al. | |
| 6,258,084 B1 | 7/2001 | Goldman et al. | |
| 6,263,248 B1 | 7/2001 | Farley et al. | |
| 6,270,476 B1 | 8/2001 | Santoianni et al. | |
| 6,273,883 B1 | 8/2001 | Furumoto | |
| 6,290,675 B1 | 9/2001 | Vujanic et al. | |
| 6,346,105 B1 | 2/2002 | Tu et al. | |
| 6,361,496 B1 | 3/2002 | Zikorus et al. | |
| 6,398,777 B1 | 6/2002 | Navarro et al. | |
| 6,413,253 B1 | 7/2002 | Koop et al. | |
| 6,451,007 B1 | 9/2002 | Koop et al. | |
| 6,451,044 B1 | 9/2002 | Naghavi et al. | |
| 6,520,975 B2 | 2/2003 | Branco | |
| 6,626,899 B2 | 9/2003 | Houser et al. | |
| 6,638,273 B1 | 10/2003 | Farley et al. | |
| 6,986,766 B2 * | 1/2006 | Caldera .................. | A61B 18/22 128/898 |
| 7,524,316 B2 * | 4/2009 | Hennings ............... | A61B 18/24 128/898 |
| 2003/0236517 A1 * | 12/2003 | Appling ........................... 606/7 | |
| 2004/0010248 A1 | 1/2004 | Appling et al. | |
| 2005/0015123 A1 * | 1/2005 | Paithankar ............. | A61B 18/24 607/88 |
| 2006/0069417 A1 * | 3/2006 | Farley et al. .................. 607/101 | |

OTHER PUBLICATIONS

Chang et al.; Endovenous Laser Photocoagulation (EVLP) for Varicose Veins; Lasers in Surgery and Medicine 31:257-262 (2002); 6 pages.
Weiss et al.; Endovenous Closure of the Greater Saphenous Vein with Radio-frequency or Laser; Cosmetic Surgery Text 2003; 26 pages.
Weiss et al.; Controlled Radiofrequency Endovenous Occlusion Using a Unique Radiofrequency Catheter Under Duplex Guidance to Eliminate Saphenous Varicose Vein Reflux: A 2-Year Follow Up; American Society for Dermatologic Surgery, Inc. 2002; 5 pages.
Goldman et al.; Intravascular 1320nm Laser Closure of the Great Saphenous Vein: A 6-12 Month Follow-up Study; Dermatology/ Cosmetic Laser Associates of La Jolla, Inc.: 28 pages.
Goldman et al.; Intravascular 1320nm Laser Closure of the Great Saphenous Vein: A 6 Month Follow-up Study; Dermatology/Cosmetic Laser Associates of La Jolla, Inc.: 26 pages.
Goldman; Endovenous Nd: YAG 1320nm Laser Treatment of the Greater Saphenous Vein: A Preliminary Study on 12 legs; Dermatology/Cosmetic Laser Associates of La Jolla, Inc.;15 pages.
Goldman et al.; Endovenous 1064-nm and 1320-nm Nd: YAG Laser Treatment of the Porcine Greater Saphenous Vein; Cosmetic Dermatology; Feb. 2003; 4 pages.
U.S. Appl. No. 09/135,330, filed Jul. 18, 1998.
U.S. Appl. No. 09/934,356, filed Aug. 21, 2001.
U.S. Appl. No. 10/160,519, filed May 31, 2002.
U.S. Appl. No. 10/351,273, filed Jan. 24, 2003.

* cited by examiner

100

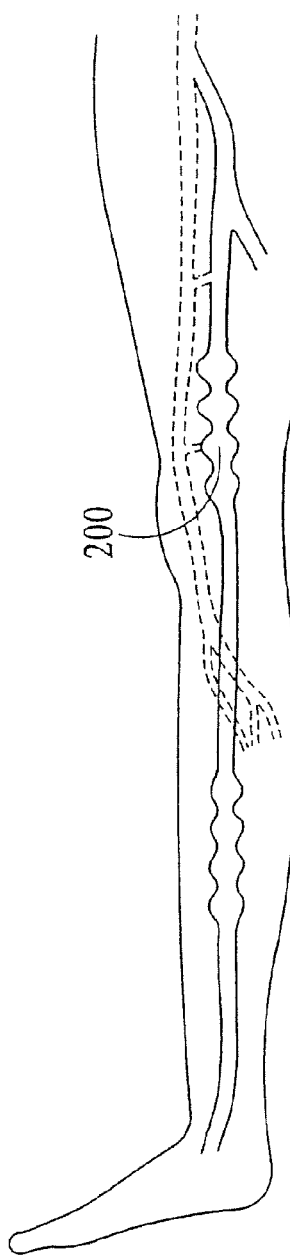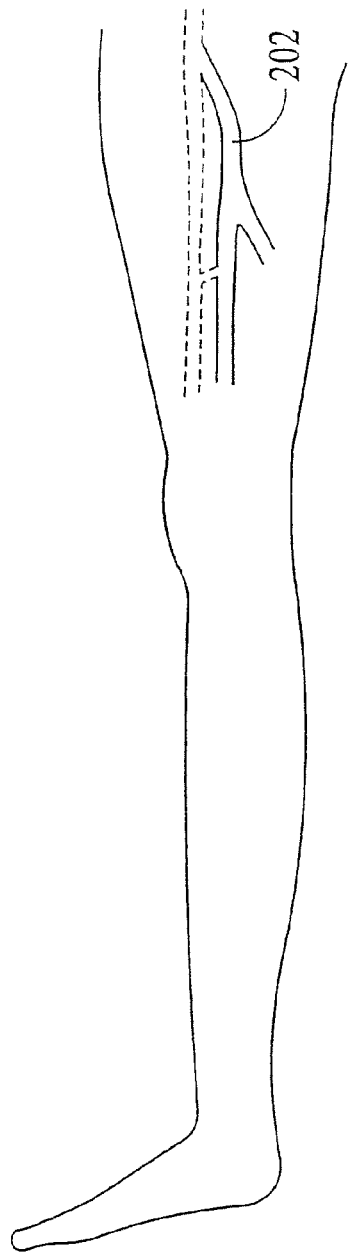
FIG. 2A
FIG. 2B

SYSTEM AND METHOD FOR ENDOVENOUS TREATMENT OF VARICOSE VEINS WITH MID INFRARED LASER

RELATED APPLICATIONS

This application is related to U.S. Provisional Patent Application Ser. No. 60/422,566 filed Oct. 31, 2002 entitled ENDOVENOUS CLOSURE OF VARICOSE VEINS WITH MID INFRARED LASER, and is a continuation of U.S. application Ser. No. 10/699,212, filed Oct. 30, 2003, now abandoned, and is related to U.S. application Ser. No. 10/982,504, filed Nov. 4, 2004, now U.S. Pat. No. 7,524,316, U.S. application Ser. No. 11/562,944, filed Nov. 22, 2006, U.S. application Ser. No. 11/612,324, filed Dec. 18, 2006, U.S. application Ser. No. 12/877,885, filed Sep. 8, 2010, and U.S. application Ser. No. 13/463,750, filed May 13, 2012, now U.S. Pat. No. 8,409,183, which are incorporated herein by reference in its entirety, and claims any and all benefits to which it is entitled therefrom.

FIELD OF THE INVENTION

The present invention relates generally laser assisted method and apparatus for treatment of varicose veins, and more particularly, to an improved catheter method and apparatus to target blood vessel walls directly and with a controlled amount of the appropriate type of energy using a motorized pull-back device.

BACKGROUND OF THE INVENTION

Most prior techniques to treat varicose veins have attempted to heat the vessel by targeting the hemoglobin in the blood and then having the heat transfer to the vessel wall. Lasers emitting wavelengths of 500 to 1100 nm have been used for this purpose from both inside the vessel and through the skin. Attempts have been made to optimize the laser energy absorption by utilizing local absorption peaks of hemoglobin at 810, 940, 980 and 1064 nm. RF technology has been used to try to heat the vessel wall directly but this technique requires expensive and complicated catheters to deliver electrical energy in direct contact with the vessel wall. Other lasers at 810 nm and 106 um have been used in attempts to penetrate the skin and heat the vessel but they also have the disadvantage of substantial hemoglobin absorption which limits the efficiency of heat transfer to the vessel wall, or in the cases where the vessel is drained of blood prior to treatment of excessive transmission through the wall and damage to surrounding tissue. All of these prior techniques result in poor efficiency in heating the collagen in the wall and destroying the endothelial cells.

Baumgardner U.S. Pat. No. 5,820,626 and Anderson U.S. Pat. No. 5,810,801 teach the advantages of using the mid IR region of optical spectrum 1.2 to 1.8 um, to heat and shrink collagen in the dermis.

The prior art teaches manual retraction of the catheter. This is a major cause of overheating and perforation of the vessel wall as even the best surgeon may have difficulty retracting the fiber at exactly the correct speed to maintain a vessel wall heating temperature of 85 deg C. Other prior art using thermocouples at the tip of the catheter depend on electrical contact between electrodes inside the vessel and are expensive and require very slow catheter-withdrawal (2 cm/min.) and are difficult to use.

The relevant references in the prior art teach use of much higher power levels, such as between about 10 to about 20 watts. This is because the prior art laser wavelengths are not as efficiently coupled to the vessel wall and are instead absorbed in the blood or transmitted through the wall into surrounding tissue. It will be understood that methods taught in the prior art can be inefficient to such a degree that external cooling is mandatory on the skin surface to prevent burns.

Finally, the methods and apparatus taught in the prior art does not mention the use of diffusing catheter tips for varicose vein treatment. Use of common, standard, non-diffusing tip fiber optic and other laser delivery devices increases the risk for perforation of the cannulated vessel.

Navarro et al., U.S. Pat. No. 6,398,777 issued Jun. 4, 2002, teaches a device and method of treating varicose veins that involves using a laser whose wavelength is 500 to 1100 nm and is poorly absorbed by the vessel wall. Laser energy of wavelengths from 500 to 1100 nm will penetrate 10 to 100 mm in tissue unless stopped by an absorbing chromophore. See FIG. 10. Most of the energy used by this method passes through the vessel wall and causes damage to surrounding tissue. Procedures using these wavelengths can require cooling of the surface of the leg to prevent burning caused by transmitted energy. Operative complications of this technique include bruising and extensive pain caused by transmitted energy and damage to surrounding tissue.

However, this technique does appear to be clinically effective because the blood that remains in the vein after compression absorbs the 500 to 1100 nm energy. 500 to 1100 nm light is absorbed in less than 1 mm in the presence of hemoglobin. See FIG. 10. This blood heats up and damages the vein wall by conduction, not by direct wall absorption as claimed by Navarro.

This prior art technique is poorly controlled because the amount of residual blood in the vein can vary dramatically. During an actual procedure using 500 to 1100 nm lasers it is possible to see the effects of blood absorption of the energy. At uncontrolled intervals white flashes will be seen indicating places of higher blood concentration. The blood can boil and explode in the vessel causing occasional perforation of the vein wall and unnecessary damage to healthy tissue.

In places without residual blood the laser energy has no absorbing chromophore and will be transmitted through the wall without causing the necessary damage and shrinkage claimed by the inventors.

Navarro claims that the treatment device described must be in direct "intraluminal contact with a wall of said blood vessel". This is necessary because the 500 to 1100 nm laser cannot penetrate any significant amount of blood, even though it requires a thin layer of blood to absorb and conduct heat to the vessel wall. This is very difficult to achieve and control.

Navarro also claims the delivery of energy in bursts. This is required using their technique because they have no means to uniformly control the rate of energy delivered. Navarro teaches a method of incrementally withdrawing the laser delivery fiber optic line while a laser burst is delivered. In clinical practice this is very difficult to do and results in excessive perforations and complications.

Closure of the greater saphenous vein (GSV) through an endolumenal approach with radiofrequency (RF) or lasers has been proven to be safe and effective in multiple studies. These endovenous occlusion techniques are less invasive alternatives to saphenofemoral ligation and/or stripping. They are typically performed under local anesthesia with patients returning to normal activities within 1-2 days.

RF energy can be delivered through a specially designed endovenous electrode with microprocessor control to accomplish controlled heating of the vessel wall, causing vein shrinkage or occlusion by contraction of venous wall collagen. Heating is limited to 85° C. avoiding boiling, vaporization and carbonization of tissues. In addition, heating the endothelial wall to 85° C. results in heating the vein media to approximately 65° C. which has been demonstrated to contract collagen. Electrode mediated RF vessel wall ablation is a self-limiting process. As coagulation of tissue occurs, there is a marked decrease in impedance that limits heat generation.

Presently available lasers to treat varicose veins endoluminally heat the vessel by targeting the hemoglobin in the blood with heat transfer to the vessel wall. Lasers emitting wavelengths of 500 to 1064 nm have been used for this purpose from both inside the vessel and through the skin. Attempts have been made to optimize the laser energy absorption by utilizing local absorption peaks of hemoglobin at 810, 940, 980 and 1064 nm. The endovenous laser treatment (EVLT™) of the present invention allows delivery of laser energy directly into the blood vessel lumen in order to produce endothelial and vein wall damage with subsequent fibrosis. It is presumed that destruction of the GSV with laser energy is caused by thermal denaturization. The presumed target is intravascular red blood cell absorption of laser energy. However, thermal damage with resorption of the GSV has also been seen in veins emptied of blood. Therefore, direct thermal effects on the vein wall probably also occur. The extent of thermal injury to tissue is strongly dependent on the amount and duration of heat the tissue is exposed to. When veins are, devoid of blood, vessel wall rupture occurs.

One in vitro study model has predicted that thermal gas production by laser heating of blood in a 6 mm tube results in 6 mm of thermal damage. This study used a 940-nm-diode laser with multiple. 1 5Jr.~second pulses to treat the GSV. Histologic examination of one excised vein demonstrated thermal damage along the entire treated vein with evidence of perforations at the point of laser application described as "explosive-like" photo-disruption of the vein wall. Since a 940 nm laser beam can only penetrate 0.03 mm in blood (17), the formation of steam bubbles is the probable mechanism of action.

Initial reports have shown endovenous RF to have excellent short-term efficacy in the treatment of the incompetent GSV, with 96% or higher occlusion at 1-3 years with a less than 1% incidence of transient paresthesia or erythema (10-11). Although most patients experience some degree of post-operative ecchymosis and discomfort, no other major or minor complications have been reported.

Patients treated with EVLT have shown an increase in post-treatment purpura and tenderness. Most patients do not return to complete functional normality for 2-3 days as opposed to the 1-day "down-time" with RF Closure™ of the GSV. Since the anesthetic and access techniques for the 2 procedures are identical, it is believed that non-specific perivascular thermal damage is the probable cause for this increased tenderness. In addition, recent studies suggest that pulsed laser treatment with its increased risk for vein perforation may be responsible for the increase symptoms with EVLT vs RF treatment. Slow uncontrolled pull-back of the catheter is likely one cause for overheating and perforation of the vessel wall as even the best surgeon may have difficulty retracting the fiber at exactly the correct speed to maintain a vessel wall heating temperature of 85° C. This technique prevents damage to surrounding tissue and perforation of the vessel.

ADVANTAGES AND SUMMARY OF THE INVENTION

This invention is a method and device to treat varicose veins by targeting the vessel wall directly with a more appropriate wavelength of laser light and controlling that energy precisely using a motorized pull back device, diffuse fiber delivery systems and utilizing thermal feedback of the treated tissue. This technique allows less energy to be used and helps prevent damage to surrounding tissue and perforation of the vessel.

It is an object and an advantage of the present invention to provide an improved method and device that uses a laser wavelength that transmits through any residual blood in the vessels and is absorbed by the water and collagen of the vessel wall. This new technique is more predicable and controllable in the presence of residual blood and is more effective in targeting only the vessel wall.

Clinical experiments have demonstrated that perforation of the vessel wall does not occur using 1.2 to 1.8 um energy, even if the fiber remains at one location for several seconds. This is because the laser energy is uniformly and predictably absorbed without any hot spots, boiling, or explosions caused by blood pockets.

Clinical experiments have demonstrated a much lower incidence of pain and collateral bruising using 1.2 to 1.8 um laser energy because the vessel wall always stops the energy. Very little transmits outside the vessel to cause damage.

Clinical experiments have demonstrated the coagulation of side vessels concurrently with larger vessel treatment due to a wave guiding effect of the 1.2 to 1.8 urn laser energy into the smaller vessels. This has not been observed using 500 to 1100 nm laser energy because residual blood will absorb and stop any energy from getting into the branch vessels.

The present improved device and method in contrast to the teachings of the prior art does not require direct intraluminal contact with the vessel wall because it is less affected by residual blood. The energy passes through the residual blood without boiling or exploding and is absorbed primarily by the vessel wall. This is a significant clinical improvement over the methods of the prior art, with much better control and predictability.

The present improved device and method utilize a continuously running laser and energy delivery with a continuous controlled withdrawal rate using a motorized pull back device.

Clinical results have shown this device and method to be clearly superior. It is easier to do for less experienced surgeons and helps eliminate perforations, pain and bruising.

Numerous other advantages and features of the present invention will become readily apparent from the following detailed description of the invention and the embodiments thereof, from the claims and from the accompanying drawings.

BRIEF DESCRIPTION OF THE DRAWINGS

FIG. 2A is a representative view of varicosed veins 200 to be treated according to the preferred embodiment of the method and apparatus of the present invention.

FIG. 2B is a representative-view of the GSV 202 to be treated according to the preferred embodiment of the method and apparatus of the present invention.

DETAILED DESCRIPTION OF THE PREFERRED EMBODIMENT

Figure 1:
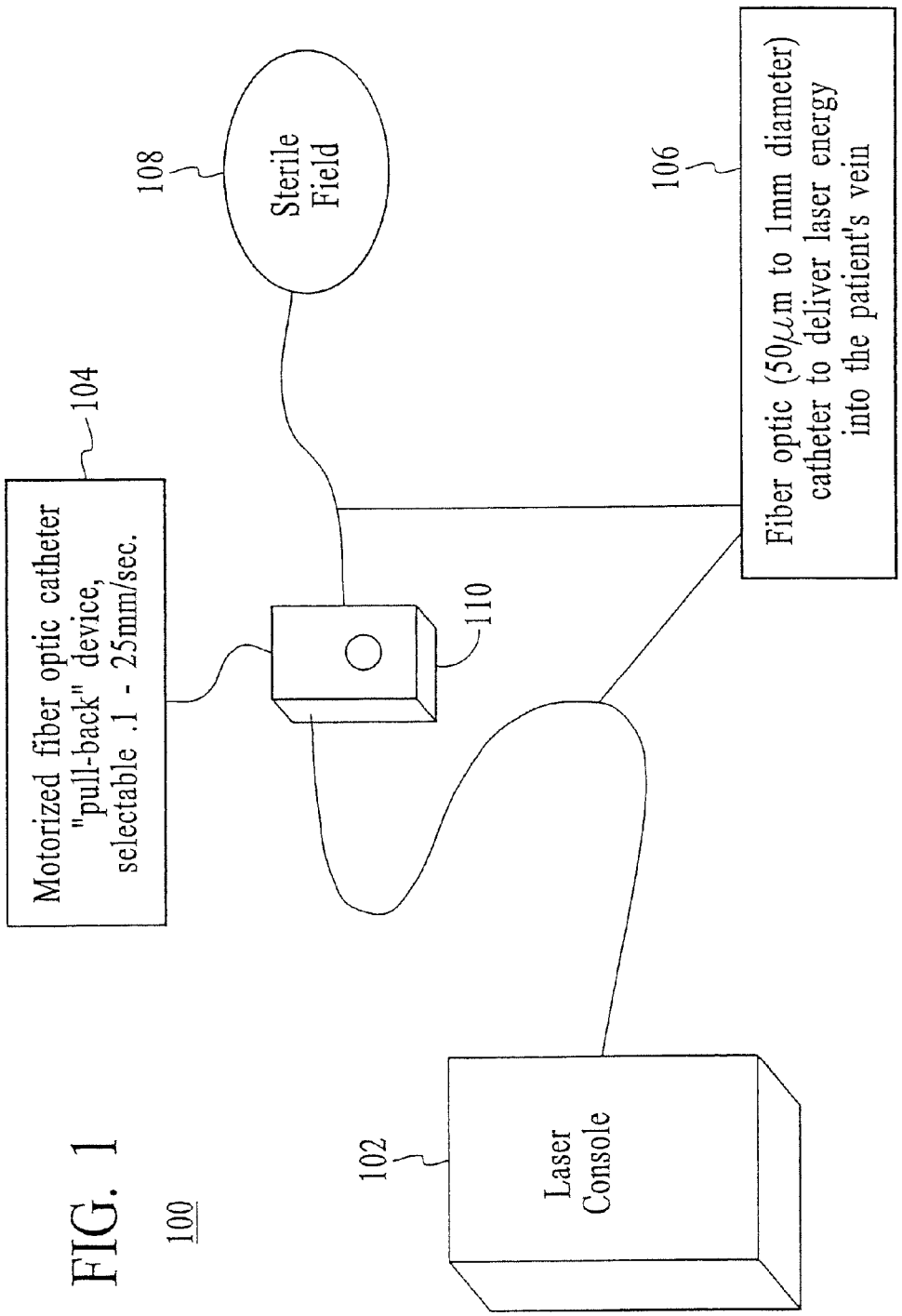
FIG. 1 is a representative schematic block diagram of a preferred embodiment of the apparatus 100 of the present invention for performing a preferred embodiment of the varicose vein closure procedure of the present invention.

The description that follows is presented to enable one skilled in the art to make and use the present invention, and is provided in the context of a particular application and its requirements. Various modifications to the disclosed embodiments will be apparent to those skilled in the art, and the general principals discussed below may be applied to other embodiments and applications without departing from the scope and spirit of the invention. Therefore, the invention is not intended to be limited to the embodiments disclosed, but the invention is to be given the largest possible scope which is consistent with the principals and features described herein.

It will be understood that in the event parts of different embodiments have similar functions or uses, they may have been given similar or identical reference numerals and descriptions. It will be, understood that such duplication of reference numerals is intended solely for efficiency and ease of understanding the present invention, and are not to be construed as limiting in any way, or as implying that the various embodiments themselves are identical.

FIG. 1 is a representative schematic block diagram of a preferred embodiment of the apparatus 100 of the present invention for performing a preferred embodiment of the varicose vein closure procedure of the present invention. As shown, the system 100 of the present invention includes a laser console 102, a motorized, fiber optic catheter "pullback" machine 104, a fiber optic catheter or other laser delivery device 106 to deliver laser energy into the patient's vein, a sterile field 108 and a controller 110.

FIG. 2A is a representative view of varicosed veins 200 to be treated according to the preferred embodiment of the method and apparatus of the present invention.

FIG. 2B is a representative view of the GSV 202 to be treated according to the preferred embodiment of the method and apparatus of the present invention.

Figure 3A:
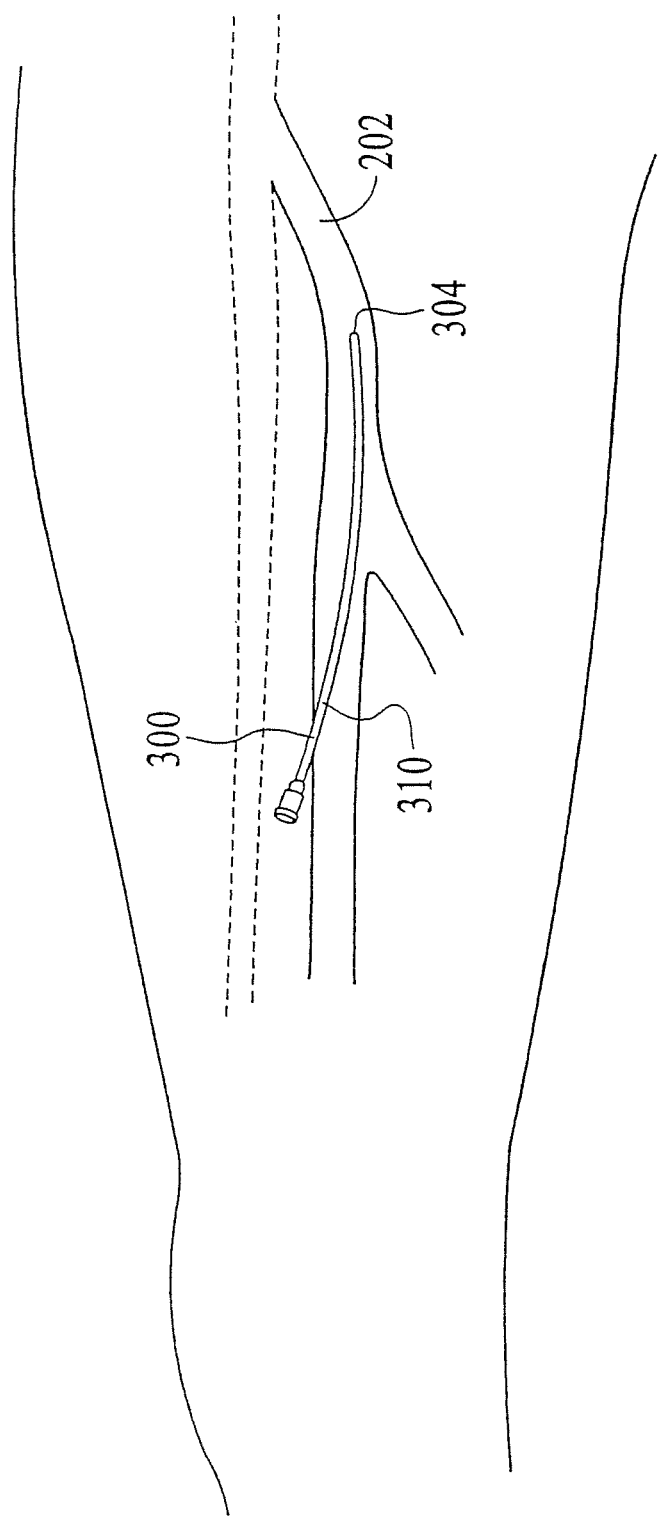
FIG. 3A is a representative view showing the beginning of the introducer or dilator 300 for percutaneous access according to the preferred embodiment of the method and apparatus of the present invention.

FIG. 3A is a representative view showing the beginning of the introducer or dilator 300 for percutaneous access according to the preferred embodiment of the method and apparatus of the present invention.

Figure 3B:
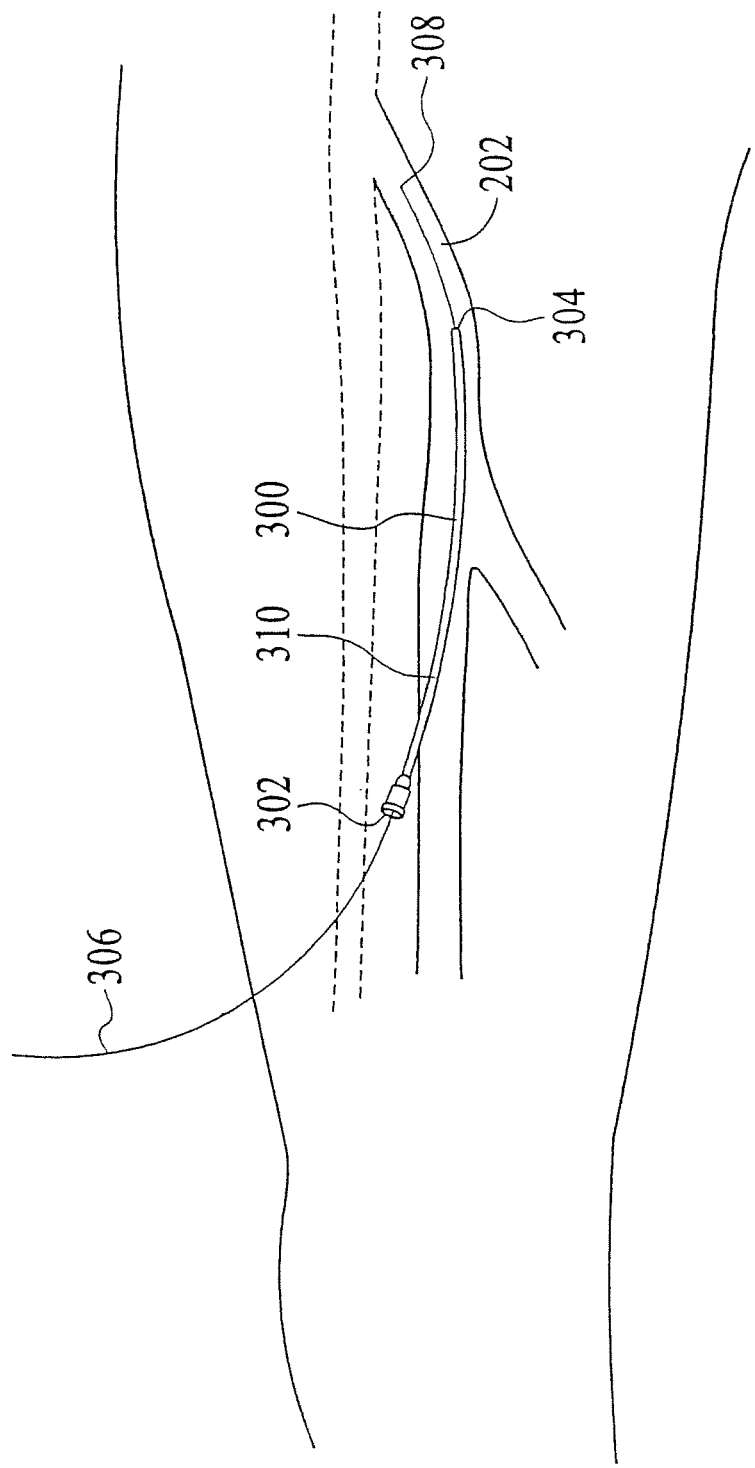
FIG. 3B is a representative view showing the use of the introducer or dilator 300 with the laser fiber 306 passing through the lumen 302 of the dilator 300 and into the GSV 202 according to the preferred embodiment of the method and apparatus of the present invention.

FIG. 3B is a representative view showing the use of the introducer or dilator 300 with the laser fiber 306 having tip 308 passing through the lumen 302 of the dilator 300 and into the GSV 202 according to the preferred embodiment of the method and apparatus of the present invention.

Figure 4:
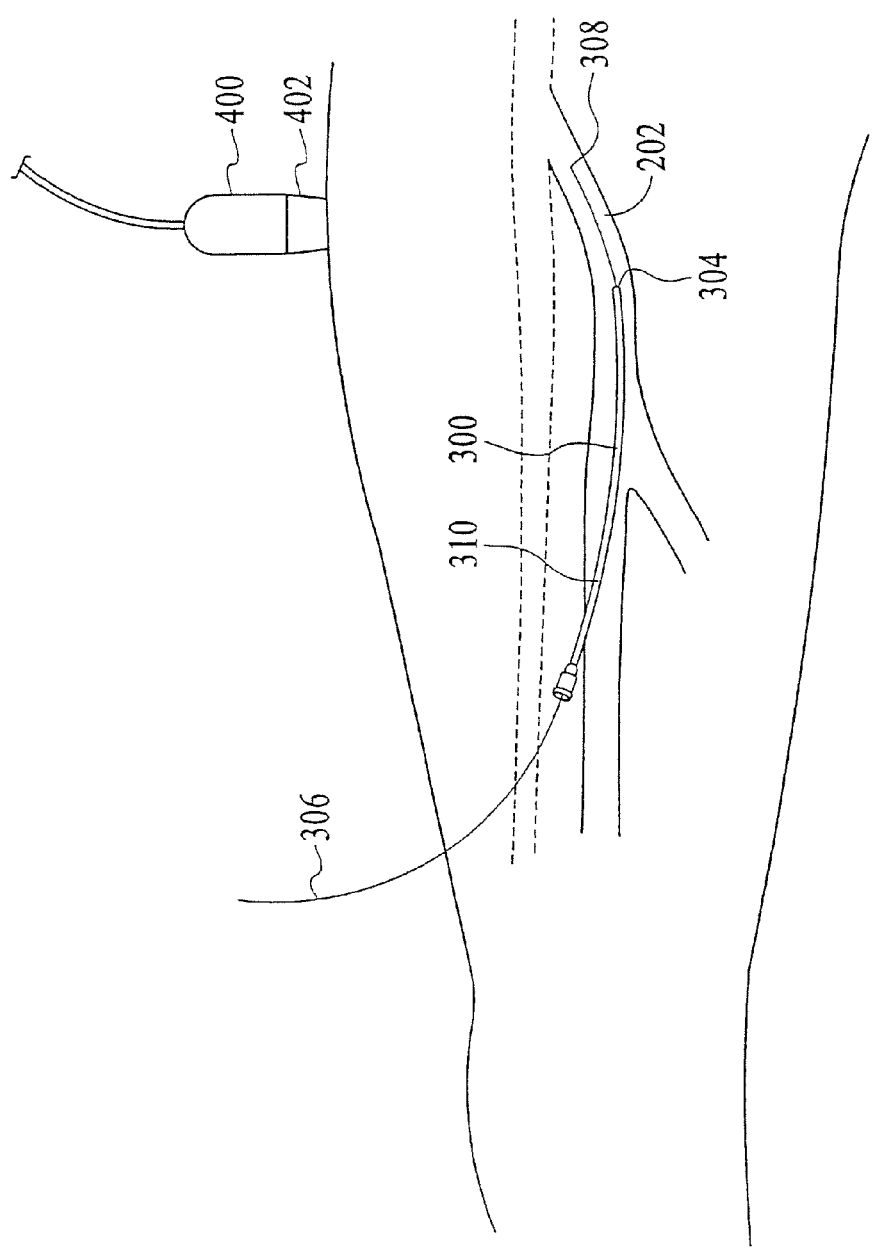
FIG. 4 is a representative view of the use of an ultrasound device 400 according to the preferred embodiment of the method and apparatus of the present invention.

FIG. 4 is a representative view of the use of an ultrasound device 400 according to the preferred embodiment of the method and apparatus of the present invention.

Figure 5:
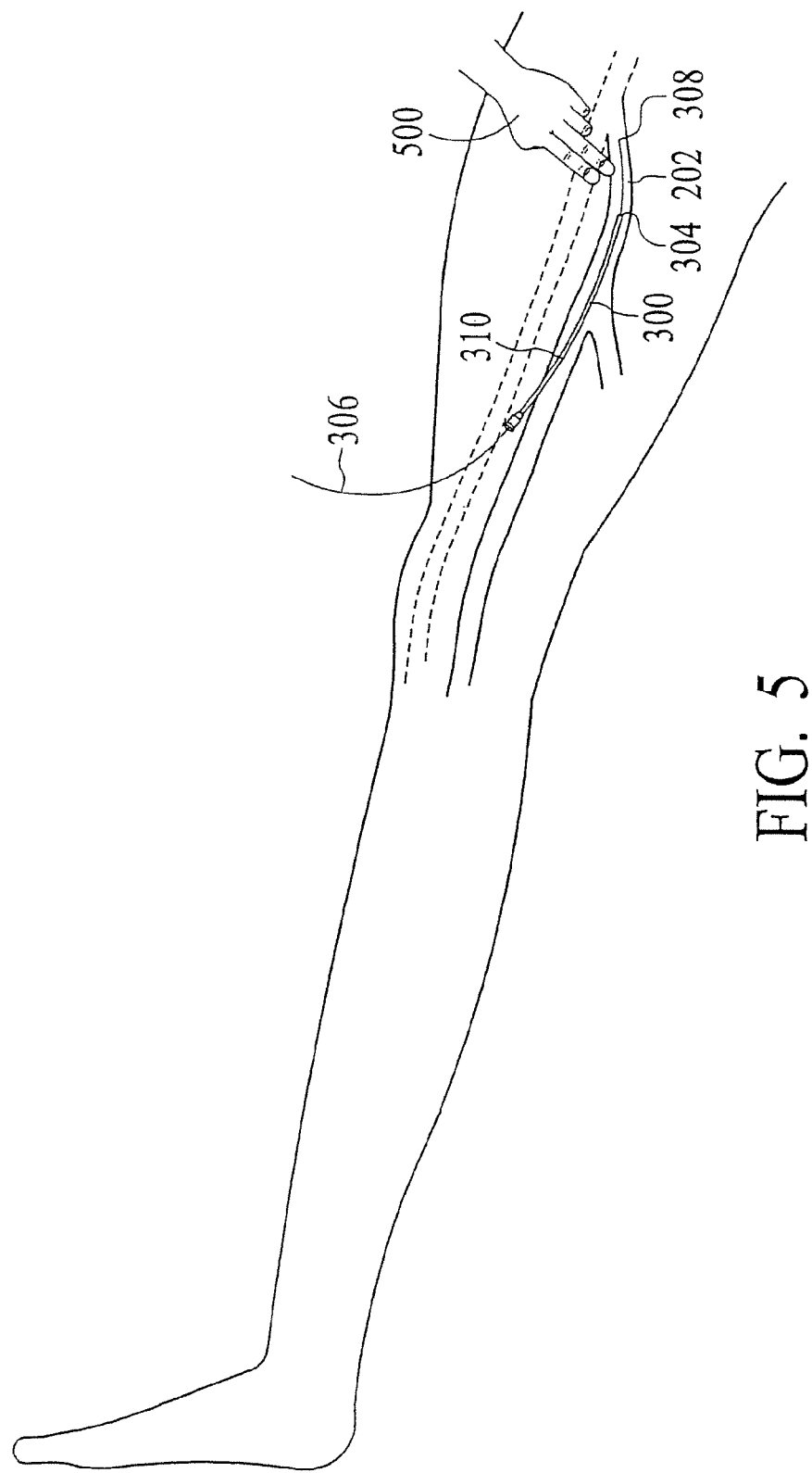
FIG. 5 is a representative view of a physician 500 performing manual compression of tissue near the tip 308 of the fiber 306 according to the preferred embodiment of the method and apparatus of the present invention.

FIG. 5 shows manual compression being applied to the patient's leg near laser tip 308.

Figure 6:
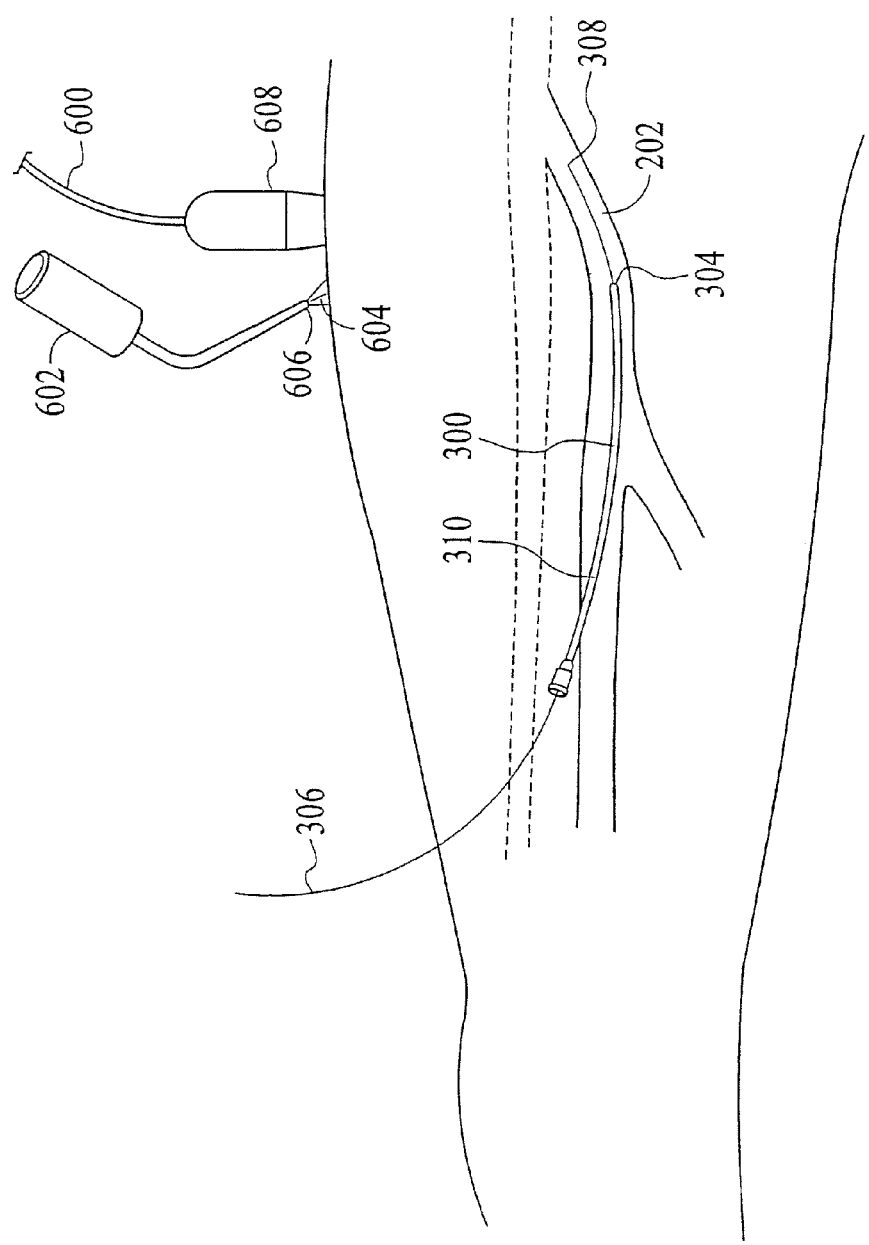
FIG. 6 is a representative view of the non-contact thermal sensor 600 and the cooling system 602 of the preferred embodiment of the method and apparatus of the present invention.

FIG. 6 shows the use of a thermal sensor device 600 having a sensor 608 together with a cooling system 620 including nozzle 606 which dispenses cooling fluid 604.

Figure 7:
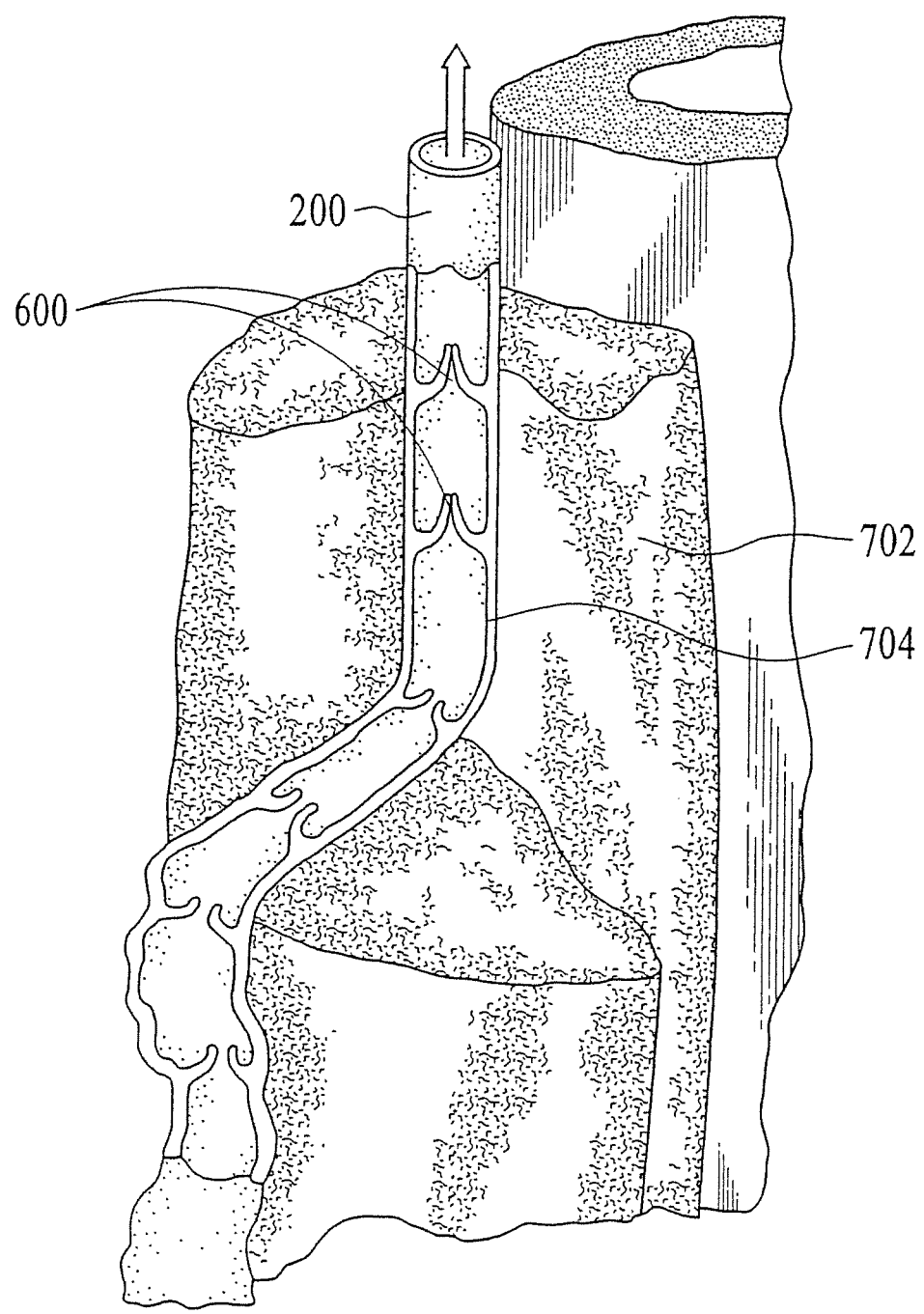
FIG. 7 is a representative view of a varicosed vein 200, showing prolapsed valves 690.

FIG. 7 is a representative view of a varicosed vein 200, showing prolapsed valves 690.

Figure 8:
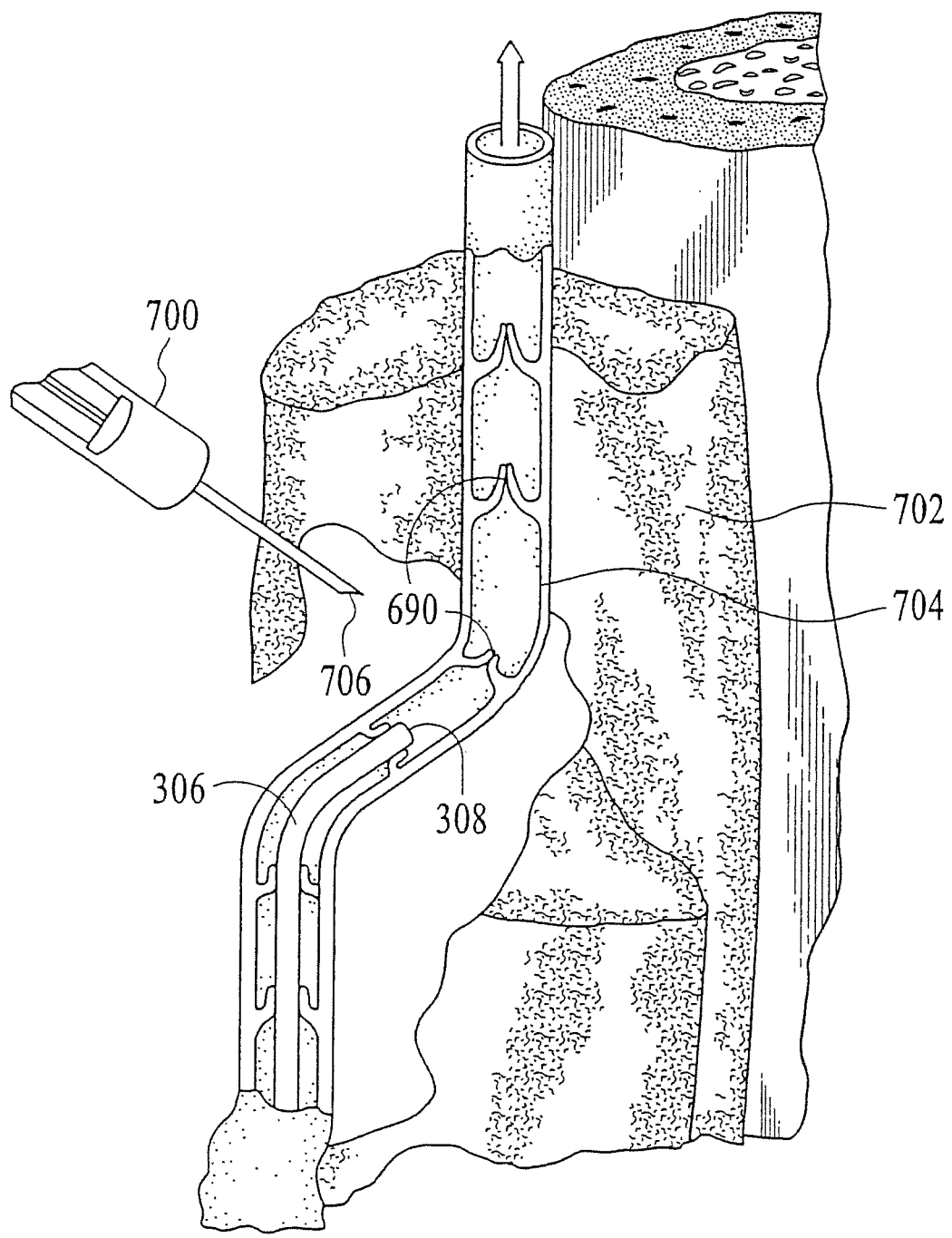
FIG. 8 is a representative view of administration of tumescent anesthesia 700 and how it compresses the vein 200 around the fiber 306 according to the preferred embodiment of the method and apparatus of the present invention.

FIG. 8 is a representative view of administration of tumescent anesthesia 700 and how it compresses the vein 200 around the fiber 306 according to the preferred embodiment of the method and apparatus of the present invention.

Prior to treatment with the laser 102, blood is removed from the vessel 200 by using tumescent anesthesia 700, typically consisting of lidocaine 0.05 to 0.1% in normal saline. Alternate compositions for tumescent anesthesia 700 will be known to those skilled in the art. A quartz or sapphire fiber optic 306 is inserted into the vein 200 via a 16 gauge needle or similar, or through the vein 200 which has been externalized through a 2-3 mm incision with a phlebectomy hook (not shown). The fiber 306 is preferably 500 to 600 um in diameter, but fibers from 50 um to 1 mm or more or less, could be used. The fiber catheter 300 is threaded through the length of the vein 200. The position of the fiber 306 within the vein 200 is noted by observing the red aiming beam of the laser 102 as it is emitted from the tip 304 of the catheter 300 and is visible through the skin. In addition, a duplex ultrasound device 400 or similar may be used to visualize the fiber tip 308 as well as the cannulated blood vessel 200 to determine vein wall contraction and closure. In a preferred embodiment of the method of the present invention, the catheter 300 must either be removed prior to pull-back, or be secured to the fiber 306 so that both the fiber 306 and the cannula or catheter 300 are retracted simultaneously.

The catheter 300 is connected to a motorized pullback device 104 either inside or outside of the sterile field 108 of the patient. The procedure begins by starting the pull back for about 2 or 3 mm and then turning the laser 102 on at about 5 watts of power. The procedure could also be done at 1 to 20 watts of power by varying the speed of the pullback device 104.

Optical absorption curves presented by Baumgardner, Anderson, and Grove U.S. Pat. No. 5,707,402 show that the primary absorbing chromophore in a vein for the 810, 940 and 1.06 um laser wavelengths is hemoglobin. When a vein is drained of blood and these lasers 102 are used, a great majority of the laser energy is transmitted through the vessel wall and heats surrounding tissue. The 1.2 to 1.8 um laser wavelengths are ideally suited to penetrate the small amount of remaining blood in the vessel 200 but also is much more strongly absorbed in the vessel wall 704 by collagen. Most of the energy is concentrated in the wall 704 for heating and shrinkage and is not transmitted through to surrounding tissue 702. This dramatically increases, the safety of the procedure. In addition these laser wavelength are considered more "eye" safe than the 800 to 1.06 um lasers, decreasing the risk of eye damage to the doctor and others in the operating arena.

In particular the Nd:YAG laser 102 or any other suitable, similar laser can be used. This laser 102 can operate at a wavelength of 1.32 um and can be either pulsed or continuous wave. This procedure works best when the laser 102 is continuous or pulsed at a high repetition rate to simulate a continuous output. The repetition rate for a pulsed laser 102 should be 10 Hz to 10,000 Hz.

Other lasers 102 such as Nd:YAP, ER:YAP, ER:YLF and others could be used to provide laser wavelengths in the 1.2 to 1.8 um region. These lasers 102 can be powered by optically pumping the laser crystal using a xenon or krypton flashlamp or laser diodes. They may be continuously pumped or pulsed using electro optical or acousto-optical shutters-or by pulsing the flashlamp itself. Lasers 102 in this wavelength region also include diode lasers that emit 1.2 to 1.8 um wavelengths directly, or fiber lasers that use a length of doped fiber optic as the lasing medium.

Cooling System with Thermal Feedback

The use of a thermocouple or infrared thermal detector 600 has been described for other applications, including on laser delivery fibers and for the treatment of varicose veins 202 using an radiofrequency heating device. However, by installing a thermocouple on the end of the laser delivery fiber optic device for the treatment of varicose veins, delivery of thermal energy can be more precisely controlled. In addition, in using fiber optic devices made of sapphire, a non-contact thermal sensor can be located in the laser console and measure tip temperature by measuring the black body infrared radiation profile emitted at the opposite end of the fiber reflected from the treatment site, typically via a beamsplitter in the laser console. A small-diameter sapphire fiber can be constructed that can be sterilized and re-used. Data obtained from the non-contact thermal sensor equipment 600 can also be used to either servo control delivery of the laser energy to maintain a certain temperature at the treatment site, or the control system can be used as a safety device, i.e., to terminate delivery of laser energy if a certain temperature is exceeded.

Another type of thermal feedback device 600 can be an external device that measures the heat that is transmitted out of the side of the vein 200 or 202 and heats up the surface of the skin 608 adjacent the treated vein 200 or 202. As described above, this detector can be either a contact thermocouple or a, non contact infrared detector 600. A particularly advantageous use of this type of thermal detection would be to automatically activate a cooling device 602, such as a cryogen spray 604, onto the skin surface to keep it cool, or to send an alarm signal to the operator of the laser that too much energy is being delivered to and escaping from the treatment site. In an optional configuration, the laser operator could point an external detector at a red aiming light that is visible through the skin from the end of the treatment, fiber, similar to the use of the ultrasound device currently used, in order to control the location and duration of the delivery of the laser energy.

FIG. 6 is a representative view of the non-contact thermal sensor 600 and the cooling system 602 of the preferred embodiment of the method and apparatus of the present invention. Non-contact thermal sensors 600 as well as contact devices, including RTDs, are well known in the art. It will be understood that the cooling device 602 can be any suitable, controlled device which allows a predetermined amount of cryogenic fluid to be dispensed from an on-board fluid reservoir or from an external/line source. In a preferred embodiment, the device 602 is computer controlled, to provide spurts or squirts of cryogenic fluid at a predetermined rate or for a predetermined duration. The cryogenic fluid 604 is dispensed onto the surface of the skin in an area adjacent the fluid dispensing nozzle 606, and the non-contact thermal sensor 600 determines the temperature of the skin in the same area 604 or in an area 608 distal from the area being cooled 604. The present invention, this application and any issued patent based hereon incorporates by reference the following issued patents with regards surface cooling methods and apparatus utilized in the present invention: U.S. patent application Ser. No. 08/692,929 filed Jul. 30, 1996, now U.S. Pat. No. 5,820,626. U.S. patent application Ser. No. 938,923 filed Sep. 26, 1997, now U.S. Pat. No. 5,976,123. U.S. patent application Ser. No. 10/185, 490 filed Nov. 3, 1998, now U.S. Pat. No. 6,413,253. U.S. patent application Ser. No. 09/364,275 filed Jul. 29, 1999, now U.S. Pat. No. 6,451,007.

Diffusing Tip Fibers

Diffusing tip fibers are well known for use with high energy lasers in other fields particularly to coagulate cancerous tumors. In addition they have been used to direct low intensity visible radiation in conjunction with photo dynamic cancer therapy. As described in the prior art, diffusing tip fibers typically require a scattering material like ceramic to be attached to the tip of a fiber in order to overcome index matching properties of the blood and liquid that the fiber is immersed into. It is frequently insufficient to abrade, roughen or shape the end of a quartz fiber by itself because the index of refraction of typical types of quartz is very close to the index of the immersing liquid, therefore any shape or structure formed in the glass or quartz portion would be ineffective in the liquid. Furthermore, in a preferred embodiment, there must be an air gap in the tip somewhere. In an alternate construction, material is selected that has bulk light scattering characteristics, like most ceramics, i.e., light is scattered as it passes through the material, as opposed to simply providing surface scattering properties. The use of diffusing tip fibers for the treatment of varicose veins is unique and has not been previously described.

Use of diffusing tip fibers for treatment of varicose veins are an improvement because the laser radiation can be directed laterally from the end of the fiber allowing more precise heating and destruction of the vein endothelial cells. Non-diffusing fiber tips direct energy along the axis of the vein and often require that the vein be compressed, in a downward position as well as around the fiber, to be most effective. The procedure described herein will work with either diffusing or non diffusing tip fibers, however, diffuse radiation will provide a more uniform and predictable shrinkage of the vein.

Adding a ceramic or quartz cap to the end of a small fiber will also aid in inserting the fiber in the vein. The cap can be made smooth and rounded so that the fiber tip does not catch on the vein or on valves within the vein as it is being inserted. A cap or smooth tip also reduces the chance of perforating the vein with a sharp fiber tip.

Figure 9A:
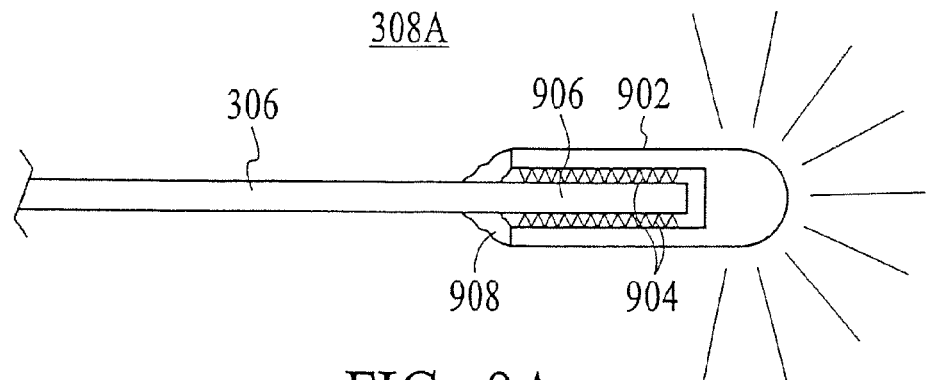
FIG. 9A is a representative view of a diffusing fiber tip according to the preferred embodiment of the method and apparatus of the present invention.

FIG. 9A is a representative view of a diffusing fiber tip 308A according to the preferred embodiment of the method and apparatus of the present invention. A ceramic or other suitable material diffusing tip 902 has an internal screw thread 904 which screws onto a buffer portion 906 of the fiber optic laser delivery device 306. The threaded portion 904 can be replaced with a clip portion or any, other suitable mechanical connection. Optionally, a non-toxic, heat-resistant-or other suitable epoxy 908 is used to permanently or removably mount the diffusing tip 902 to the fiber optic laser delivery device 306. The epoxy 908 can also be an adhesive, a bonding agent or joining compound, etc.

Figure 9B:
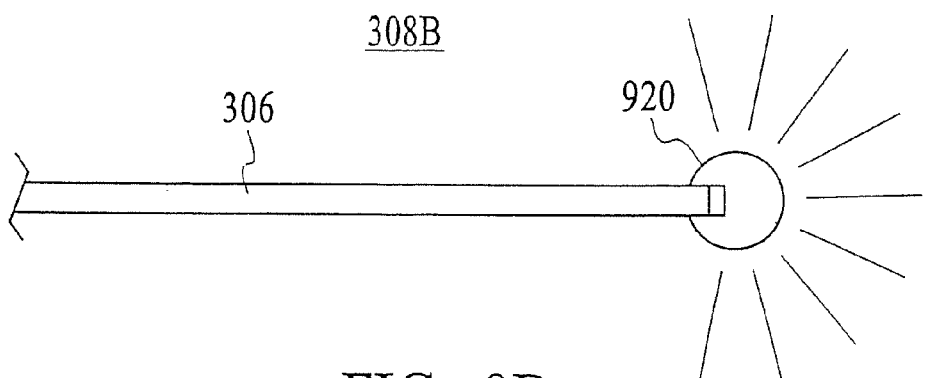
FIG. 9B is a representative view of another diffusing fiber tip according to the preferred embodiment of the method and apparatus of the present invention.

FIG. 9B is a representative view of another diffusing fiber tip 308B according to the preferred embodiment of the method and apparatus of the present invention. As shown, a small, circular diffusing bead or head 920 formed of ceramic or other suitable, appropriate material is coupled to the fiber optic laser delivery device 306. Optionally, a non-toxic, heat-resistant or other suitable epoxy 908 is used to permanently or removably mount the diffusing tip 920 to the fiber optic laser delivery device 306.

Figure 9C:
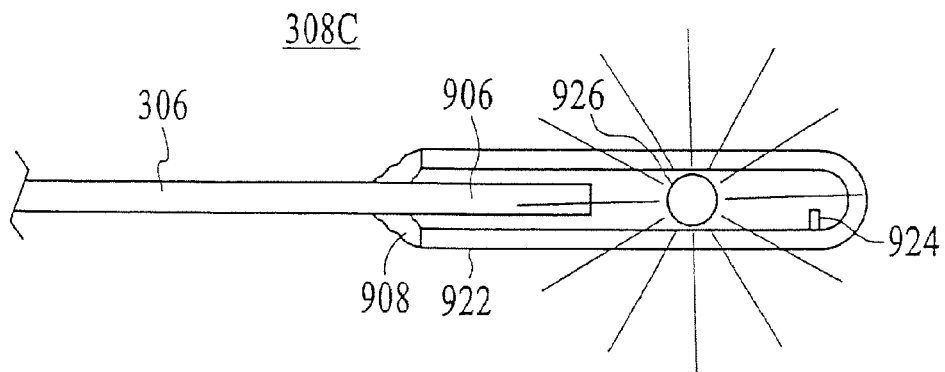
FIG. 9C is a representative view of yet another diffusing fiber tip according to the preferred embodiment of the method and apparatus of the present invention.

FIG. 9C is a representative view of yet another diffusing fiber tip 308C according to the preferred embodiment of the method and apparatus of the present invention. In this embodiment, a quartz tube 922 is placed over the distal end 906 of the optical fiber laser delivery device 306, thereby forming a sealed air chamber 924. Optionally, a spherical or other shaped diffusing ball 926 is placed within the air chamber 924 such that electromagnetic radiation directed through the fiber optic laser delivery device 306 is diffused as it is delivered from the tip 922 of the device 308C. Optionally, a non-toxic, heat. resistant or other suitable epoxy 908 or other suitable attachment means is used to permanently or removably mount the quartz capillary tube 922 to the fiber optic laser delivery device 306.

Figure 10:
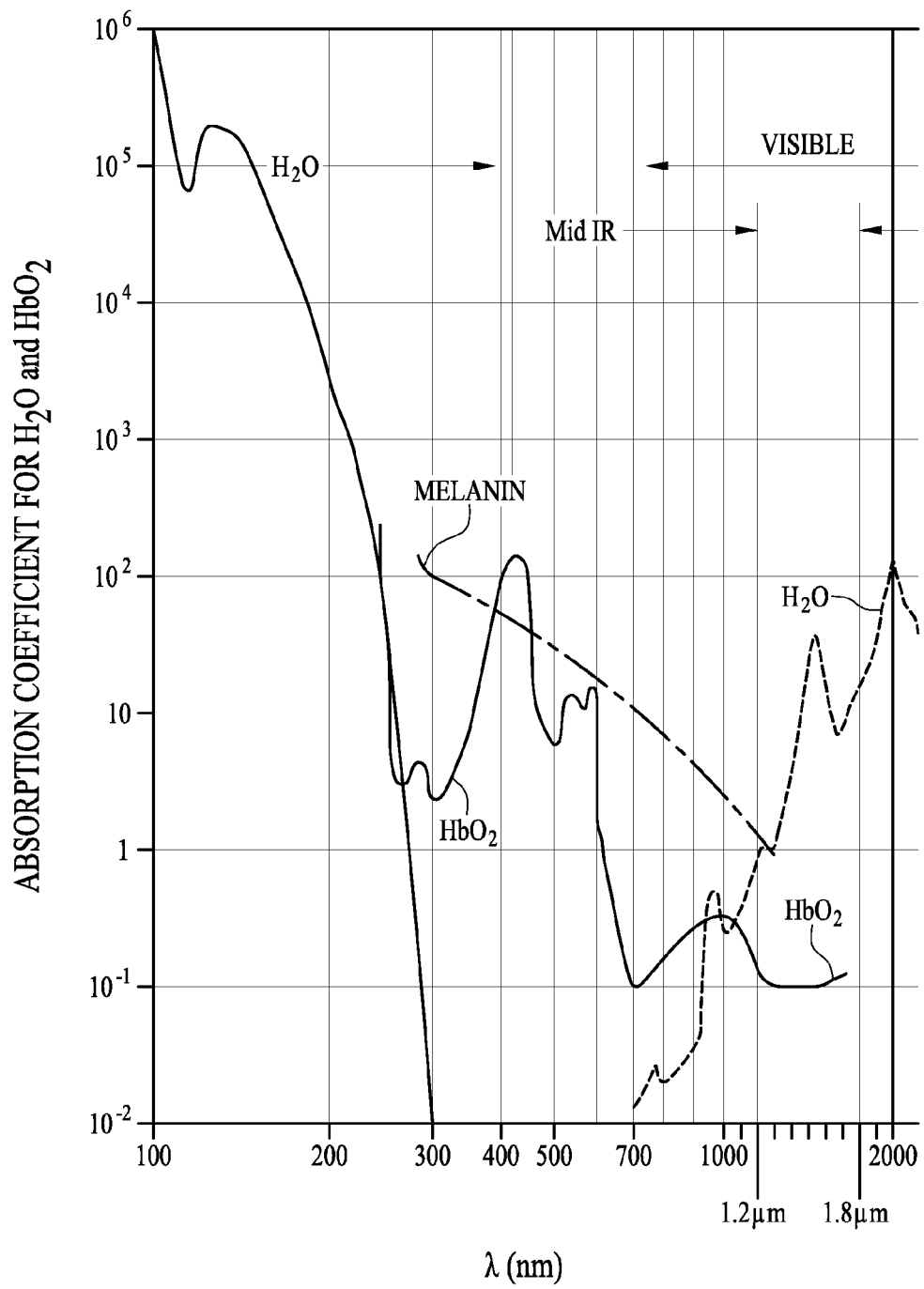
FIG. 10 shows curves for absorption coefficients of melanin, hemoglobin and water as a function of wavelength according to the preferred embodiment of the method and apparatus of the present invention.

FIG. 10 shows curves for absorption coefficients of melanin, hemoglobin and water as a function of wavelength according to the preferred embodiment of the method and apparatus of the present invention. It will be observed in FIG. 10 that the region between about 550 nm to about 1060 nm shows high hemoglobin absorption and low water absorption, as is well known in the prior art technology. It will further be observed that the region between about 1200 nm to about 1800 nm shows low hemoglobin and higher water absorption, which is a key to the present invention.

Experimental Results

A novel endolumenal laser was evaluated in 12 incompetent greater saphenous veins in 11 patients.

Method Overview: Twelve incompetent greater saphenous veins in 11 patients were treated with a 1 320 nm "continuous" Nd:YAG laser at 5 W with an automated pull-back system at 1 mm/sec. Patients were examined at 1 week, 3, 6 and 9 months post-operatively. Ten treated veins were examined histologically.

Brief Results: Full thickness vein wall thermal damage occurred in all patients without evidence for vessel perforation. No post-operative complications or pain was noted in any patient. All patients had complete disappearance of the incompetent GSV with resolution of all pre-operative symptoms.

Brief Conclusion: The 1320 nm Nd:YAG laser is safe and effective for endovascular ablation of the incompetent greater saphenous vein.

Method: Patient characteristics are found in Table 1.

TABLE 1

Patient Characteristics:

11 patients 12 Great Saphenous Veins
10 female 1 male
Average Age: 50 (19-78)
12/12 legs had varicose and reticular veins
12/12 legs had reflux>1. sec through the saphenofemoral junction down the great saphenous vein
12/12/had leg pain
2/12 had leg edema
Great Saphenous Vein diameter 2 cm distal to saphenofemoral junction while patient is standing: 5.5-12 mm (Ave. 8.4 mm)

A 550 um quartz fiber is inserted into the vein through an externalization approach as previously described and threaded up to the saphenofemoral junction. The position of the fiber within the vein is noted by observing the red aiming beam of the laser as it is emitted from the tip of the catheter as well as through Duplex evaluation. The catheter is connected to a motorized pull back device. The procedure begins by starting the pull back for about 2 or 3 mm and then turning the laser on in a near continuous mode at 5 W at 167 mJoules given at a repetition rate of 30 Hz. All laser fibers were withdrawn with a motorized pull-back system at a rate of 1 mm/second.

The average length of treated GSV was—1.7.45+/-3 cm. Average fluence utilized was 755 Joules over 160+/-20 seconds for an average of 4.7 JIsec. Immediately after the veins were lasered, the distal 3 cm was excised, the proximal portion ligated with 3/0 vicryl suture and placed in formaldehyde for histopathologic processing and evaluation. Nine veins were evaluated by a dermatopathologist blinded to the purpose and parameters of the experiment.

Patients were seen back at 1 day, 1 week, 1, 3, 6, and 9 months post-operatively for Duplex examination. This examination was performed by a physician not involved in the surgical procedure.

Experimental Results:

All patients tolerated the procedure well without any noticeable pain or discomfort. All patients had an unremarkable post-operative course without any pain. Bruising over the course of the treated vein occurred in 2 of the 12 treated legs and resolved within 10-14 days. No evidence of superficial thrombophlebitis occurred.

Three patients with four treated legs were followed for 9 months, three patients were followed for 6 months and 5 patients were followed for 3 months.

All patients remarked on the complete resolution of preoperative pain. Of the two patients with pedal edema, one patient had total resolution of the pedal edema. The other patient—had a 75% reduction in pedal edema.

Duplex examination of the treated GSV segment demonstrated a non-compressible totally occluded vessel for 3r5 months-post-operatively in every patient. At 3 months, the thrombotic GSV was 1-4 mm in diameter smaller (approximately 50%). At 6 months, the GSV could not be identified in any patient.

Figure 11:
FIG. 11 is a photograph of experimental results showing the distal greater saphenous vein immediately after treatment with a 1320 nm Nd:YAG laser.

FIG. 11 is a photograph of experimental results showing the distal greater saphenous vein immediately after treatment with a 1320 nm Nd:YAG laser.

Table 2 describes the extent of thermal damage into the vein wall in mm of amorphous amphophilic material. In addition, the layers of vein wall exhibiting thermal damage were described. Full thickness vein wall damage occurred in all specimens.

TABLE 2

Perioperalive Diameter of the Great Saphenous Vein and Extent of Thermal Damage from intravascular 1320 nm Laser

| Pre-operative diameter | Thickness of thermal damage (amorphous amphophilic Diameter material)(mm) |
| --- | --- |
| 8.0 mm | 0.8 mm full thickness vein wall damage |
| 9.0 mm | Full thickness damage 1 mm in depth including hyperchromasia or loss of endothelial nuclei, and subendothelial necrosis |
| 8.0 mm | Full thickness damage of the vein wall to 0.33 mm of endothelial nuclei and subendothelial necrosis |
| 5.5 mm | Full thickness subendothelial damage to 0.9 mm with hyperchromasia of endothelial cells |
| 8.2 mm | 0.75 mm full thickness vein wall |
| 8.3 mm | 0.74 mm full thickness vein wall damage |
| 10 mm | 0.6 mm full thickness vein wall damage |
| 7.7 mm | 0.7 mm full thickness vein wall damage |
| 8 mm | 0.8 mm full thickness vein wall damage |

Discussion: Optical absorption curves show that the primary absorbing, chromophore in a vein for the 810, 940 and 1064 nm laser wavelengths is hemoglobin. When a vein is drained of blood and these lasers are used, a majority of the laser energy is transmitted through the vessel wall to heat surrounding tissue. The 1320 nm laser wavelength is ideally suited to penetrate the small amount of remaining blood in the vessel and is much more strongly absorbed in the vessel wall by collagen. Most of the energy is concentrated in the wall for heating and shrinkage. This study demonstrates that the 1320 nm-Nd:YAG laser with an automated pull-back system is safe and effective for endovascular laser destruction of the GSV.

Unless defined otherwise, all technical and scientific terms used herein have the same meaning as commonly understood by one of ordinary skill in the art to which the present invention belongs. Although any methods and materials similar or equivalent to those described can be used in the practice or testing of the present invention, the preferred methods and materials are now described. All publications and patent documents referenced in the present invention are incorporated herein by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

The invention claimed is:

1. An endovenous method of treating a varicose vein comprising:
    inserting a fiber optic laser delivery device into the varicose vein, the fiber optic laser delivery device having a diameter of 500 to 600 um and a laser radiation diffusing tip;
    retracting the fiber optic laser delivery device through the varicose vein using a pull-back device at a rate of 1.0 mm/sec while simultaneously delivering laser energy at a power level of 5 watts therefrom having a wavelength of 1.32 um to permanently destroy the functionality of the varicose vein; and
    measuring black body infrared radiation profile emitted at opposite end of a fiber delivery device and reflected from the treatment site to determine tip temperature.

2. The method of claim 1 in which the step of retracting the fiber optic laser delivery device is automated by using a pull-back device to retract the fiber optic laser delivery device at a rate of 1.0 mm/sec.

3. The method of claim 1 further comprising draining of blood from the varicose vein prior to treatment with laser energy.

4. The method of claim 1 in which the fiber optic laser delivery device is first introduced to the varicose vein through an introducer catheter.

5. The method of claim 1 wherein said laser is a Nd: YAG laser.

6. The method of claim 1 wherein a distal end of the fiber optic laser delivery device is provided with the diffusing tip.

7. The endovenous method according to claim 1, wherein the pull-back device is a motorized pull-back device.

8. The endovenous method according to claim 1, further comprising controlling temperature in a region near a distal end of the fiber optic laser delivery device during treatment using input from a thermal sensor.

9. The endovenous method according to claim 1 wherein the laser energy is delivered in pulses at a repetition rate of 10 Hz to 10000 Hz, and wherein the repetition rate simulates a continuous output.

10. The endovenous method according to claim 1 wherein laser radiation is directed laterally from the laser radiation diffusing tip of the fiber optic laser delivery device.

11. A system for endovenous treatment of varicose veins, the system comprising the following:
    a laser having a wavelength of 1.32 um;
    a fiber optic laser delivery device having a proximal end and a distal end, the fiber optic laser delivery device being adapted to deliver laser energy from the distal end to the wall of a varicose vein whereby the functionality of the varicose vein is destroyed and collagen in the varicose vessel wall is heated and shrunk;
    a pull-back device connected to the fiber optic laser delivery device, the pull-back device being capable of retracting the fiber optic laser delivery device through the varicose vein at a rate of 1.0 mm/sec;
    a diffusing tip fiber at the distal end of the fiber optic laser delivery device, the diffusing tip adapted to direct laser radiation laterally during treatment; and
    a non-contact thermal sensor located in a laser console to measure diffusing tip temperature by measuring the black body infrared radiation profile emitted at the opposite end of the fiber delivery device reflected from a treatment site.

12. The system of claim 11 further comprising apparatus for administration of anesthesia to tissue surrounding the varicose vein, wherein the anesthesia causes swelling of the tissue surrounding the varicose vein which causes compression of the varicose vein in order to remove an amount of blood prior to treatment.

13. The system of claim 11 further comprising an introducer catheter in which an elongated lumen portion has a proximal end and a distal end, wherein the fiber optic laser delivery device is introduced to the introducer catheter through the proximal end and is introduced to the varicose vein through the distal end.

14. The system of claim 11 wherein said laser is a Nd: YAG laser.

15. The system of claim 11 wherein the diffusing tip fiber is adapted to provide even distribution of energy radiating from the diffusing tip fiber during treatment.

16. The system according to claim 11, wherein the pull-back device is a motorized pull-back device.

17. The system of claim 11 further including a beam splitter to separate the black body infrared radiation emitted at the opposite end of the fiber delivery device reflected from the treatment site from laser radiation delivered to the treatment site.

18. An endovenous method of treating a varicose vein with laser energy to heat and shrink collagen in the vein and to destroy the functionality of the varicose vein, the method comprising:
- inserting a Nd: YAG laser delivery device into the varicose vein;
- using a diffusing fiber tip to direct laser radiation laterally from the end of the fiber and delivering laser energy having a wavelength of 1.32 um while within the varicose vein;
- retracting the laser delivery device through the varicose vein using a pullback device, thereby heating and shrinking the collagen in the vein and destroying the functionality of the varicose vein; and
- using a black body infrared radiation profile emitted at the opposite end of the laser delivery device reflected from a treatment site to control delivery of the laser energy to maintain a certain temperature at the treatment site.

19. The method of claim 18 wherein the step of retracting is performed at a rate of 1.0 mm/sec.

20. The endovenous method according to claim 18, wherein the pull-back device is a motorized pull-back device.

21. An endovenous method of treating a varicose vein comprising:
- inserting a fiber optic laser delivery device into the varicose vein, the fiber optic laser delivery device having a diameter of 400 to 600 um and a laser radiation diffusing tip;
- retracting the fiber optic laser delivery device through the varicose vein using a pull-back device at a rate of between 1.0 to and 5.0 mm/sec while simultaneously delivering laser energy at a power level of 1 to 20 watts therefrom and having a wavelength of 1.32 um to permanently destroy the functionality of the varicose vein;
- controlling temperature in a region near a distal end of the fiber optic laser delivery device during treatment using input from a non-contact thermal sensor; and
- controlling delivery of the laser energy to the fiber optic laser delivery device to control the temperature in the region near the distal end of the fiber optic laser delivery device during treatment.

22. The endovenous method according to claim 21, wherein the pull-back device is a motorized pull-back device.

* * * * *